United States Patent [19]

Cubicciotti et al.

[11] Patent Number: 4,619,895

[45] Date of Patent: Oct. 28, 1986

[54] LIPOPROTEIN MARKER FOR HYPERTRIGLYCERIDEMIA

[75] Inventors: Roger S. Cubicciotti, El Cerrito; Alexander E. Karu, Kensington; Ronald M. Krauss, Berkeley, all of Calif.

[73] Assignee: The Regents of The University of California, Berkeley, Calif.

[21] Appl. No.: 608,750

[22] Filed: May 10, 1984

[51] Int. Cl.$^4$ .................. G01N 33/577; G01N 33/535; C12N 5/00; C12N 15/00

[52] U.S. Cl. .......................................... 435/7; 435/68; 435/172.2; 435/240; 436/514; 436/518; 436/536; 436/548; 436/811; 436/815; 436/542; 935/104; 935/110; 530/837

[58] Field of Search ............... 436/514, 518, 536, 548, 436/811, 815, 542; 435/4, 7, 68, 70, 240, 948, 172.2; 935/89, 95, 104, 110; 260/112 R; 530/837

[56] References Cited

PUBLICATIONS

Teng, B. et al, *Proc. Natl. Acad. Sci., USA*, vol. 80(21), pp. 6662–6666 (1983).
Patton, J. G. et al, *J. Immunol. Methods*, vol. 55(2), pp. 193–203 (1982).
Milne, R. W. et al, *Arteriosclerosis*, vol. 3(1), pp. 23–30 (1-1983).
Milne, R. W. et al, *FEBS Lett.*, vol. 146(1), pp. 97–100 (9-1982).
Milne, R. W. et al, *J. Clin. Invest.*, vol. 68(1), pp. 111–117 (1981).
Mao, S. J. T. et al, *Clin. Chem.*, vol. 29(11), pp. 1890–1897 (1983).
Curtiss, L. K., *J. Clin. Invest.*, vol. 72(4), pp. 1427–1438 (1983).
Nelson, C. A., *J. Lipid Research*, vol. 25(8), pp. 821–830 (1984).
Patton, J. G. et al, *Clin. Chem.*, vol. 29(11), pp. 1898–1903 (1983).
Tikkanen, M. J. et al, *Arteriosclerosis*, vol. 4(2), pp. 138–146 (3-1984).
Tikkanen, M. J. et al, *J. Lipid Res.*, vol. 24(11), pp. 1494–1499 (1983).
Tikkanen, M. J. et al, *J. Lipid Res.*, vol. 23, pp. 1032–1038 (1982).
Watt, T. S. et al, *Proc. Natl. Acad. Sci. USA*, vol. 80(1), pp. 124–128 (1983).
Krauss et al. (1980) Clin. Chim. Acta. 104:275–290 "Interrelationships Among Sungroups of Serum Lipoproteins in Normal Human Subjects".
Shen et al. (1981) J. Lipid Res. 22:236–244 "Heterogeneity of Serum Low Density Lipoproteins in Normal Human Subjects".
Lindgren et al. (1981) in: "AOCS Conference on Dietary Fats and Health", Perkins and Visek, eds., Chicago, Human Serum . . . and Analysis.
Krauss and Burke (1982) J. Lipid Res. 23:97–104 "Identification of Multiple Subclasses of Plasma Low Density Lipoproteins . . . Humans".
Maciejko et al. (1983) N. Eng. J. Med. 309:385–389 "Apolipoprotein A-I as a Marker of Angiographically Assessed Coronary-Artery Disease".
Blackburn (1983) N. Eng. J. Med. 309:426–428 "The Meaning of a New Marker for Coronary-Artery Disease".
Tikkanen et al. (1982) J. Lipid Res. 23:1032–1038 "Antigenic Mapping of Human Low Density Lipoprotein with Monoclonal Antibodies".
Marcel et al. (1982) J. Biol. Chem. 257:13165–13168 "Mapping of Antigenic Determinants of Human Apolipoprotein B . . . Density Lipoproteins".
Mao et al. (1982) Biochem. Biophys. Acta 713:365–374 "Immunochemical Properties of Human Low Density Lipoproteins as . . . Antibodies".

*Primary Examiner*—Charles F. Warren
*Assistant Examiner*—Margaret Moskowitz
*Attorney, Agent, or Firm*—Leydig, Voit & Mayer

[57] ABSTRACT

Methods and compositions are provided for the detection of a particular low density lipoprotein which has been found to be a marker for patients suffering from type IV hypertriglyceridemia. A monoclonal antibody capable of specifically binding to a characteristic epitopic site on this LDL subspecies can be utilized in a wide variety of immunoassays.

Hybridoma cell line SPL.IVA5A1 was deposited at the American Type Culture Collection on Mar. 29, 1984, and granted accession no. HB 8535.

4 Claims, No Drawings

LIPOPROTEIN MARKER FOR HYPERTRIGLYCERIDEMIA

This invention was made with Government support under Contract No. N00014-81-C-0570 awarded by the Office of Naval Research. The Government has certain rights in this invention.

BACKGROUND OF THE INVENTION

1. Field of the Invention

Coronary artery disease continues to be a leading cause of death in most developed countries in the world. Although a number of prophylactic measures can reduce mortality in individuals suffering from coronary artery disease, such as dietary modification and exercise programs, it is necessary to identify those individuals who are at risk or suffering from such coronary artery disease to take advantage of these measures.

Recently, screening techniques which rely on the presence of abnormal lipoprotein serum profiles to identify individuals at risk have been developed. Such techniques, however, have not been entirely satisfactory. Extreme variability in the amount of serum lipoproteins among individuals will obscure the small differences between normal and coronary-prone patients. While absolute levels or ratios of low density lipoprotein (LDL), high density lipoprotein (HDL) and HDL-associated and LDL-associated cholesterol generally correlate with cardiovascular mortality based on average levels in the population as a whole, quantitative differences among individuals are small, standard errors are large, and the predictive value of such tests remain unproven.

It would thus be desirable to provide a reliable, rapid, and efficient technique for screening large numbers of individuals to determine individuals who are suffering from or at risk from a coronary artery disease.

2. Description of the Prior Art

Krauss et al. (1980) Clin. Chim. Acta. 104:275–290 report that serum levels of smaller slower floating low density lipoprotein (LDL) subspecies ($S_f<7$) correlate inversely with levels of high density lipoprotein (HDL). Shen et al. (1981) J. Lipid Res. 22:236–244 and Lindgren et al. (1981) in: "AOCS Conference on Dietary Fats and Health", Perkins and Visek, eds., Chicago 1981, describe the separation of six subfractions of LDL from normal subjects by equilibrium density gradient ultracentrifugation. Krauss and Burke (1982) J. Lipid Res. 23:97–104 report that discrete subpopulations of LDL in normal subjects can be differentiated on the basis of characteristic hydrated densities and particle sizes. Maciejko et al. (1983) N. Eng. J. Med. 309:385–389 describe the identification of apolipoprotein A-I as a marker for patients suffering from coronary-artery disease. Blackburn (1983) N. Eng. J. Med. 309:426–428, provides a critical discussion of the report of Maciejko et al. Monoclonal antibodies raised against LDL's, including apolipoprotein B, have been reported. See, e.g., Tikkanen et al. (1982) J. Lipid Res. 23:1032–1038; Marcel et al. (1982) J. Biol. Chem. 257:13165–13168; Mao et al. (1982) Biochem. Biophys. Acta 713:365–374; Curtiss and Edgington (1982) J. Biol. Chem. 257:15213–15221; and Tsao et al. (1982) J. Biol. Chem. 257:15222–15228.

SUMMARY OF THE INVENTION

The present invention provides a useful method for identifying patients susceptible to or suffering from Type IV hypertriglyceridemia (HTG). The method relies on the detection of a newly-recognized, immunologically-distinct low density lipoprotein (LDL) subspecies having a size in the range from about 215 to 230 Å. Detection may be accomplished by reacting a sample of the patient's serum with a monoclonal antibody specific for a unique determinant site on the particular LDL subspecies. An LDL fraction may be isolated from the serum sample prior to reaction with the antibody, or the serum sample may be reacted without prior separation.

DESCRIPTION OF THE SPECIFIC EMBODIMENTS

Methods and compositions are provided for the identification of patients suffering from Type IV hypertriglyceridemia (HTG). A serum assay is utilized to detect the presence of a particular low density lipoprotein (LDL) subspecies which is characteristic of patients suffering from the disease. Conveniently, the lipoprotein is detected by means of monoclonal antibodies specific for an epitopic site on the lipoprotein which distinguishes it from other LDL present in the serum of normal individuals.

The characteristic low density lipoprotein subspecies comprises abnormally small LDL particles having a diameter in the range from 215 to 230Å, a flotation rate in the range from 0.0 to 0.3 S, and a buoyant density in the range from 1.050 to 1.063 g/ml. While trace amounts of lipoprotein having similar physical characteristics may be infrequently observed in clinically normal individuals, it has been found that the LDL particle characteristic of HTG is immunologically distinguishable from any similar subspecies occurring in normal individuals. In particular, the characteristic LDL subspecies has been found to possess at least one unique determinant site not possessed by LDL subspecies in normal individuals, which unique determinant site may be used to identify its presence in serum.

The LDL subspecies of the present invention can be detected using various immunological assays. Such assays require the use of monoclonal antibodies capable of detecting a unique determinant site on the LDL. Antigens suitable for use in preparing such monoclonal antibodies may be obtained from patient sera having the particular LDL present. Typically, an LDL fraction in the size range of interest can be obtained from patient sera by analytic centrifugation and gel electrophoresis, as taught in the Experimental section of the present application.

Surprisingly, the antigen used for immunization in the Experimental section herein was obtained from an apparently normal individual. The individual's serum, however, contained an LDL subspecies having physical characteristics within the range expected for the characteristic subspecies of the present invention.

Once a sufficient amount of antigen has been obtained, monoclonal antibodies can be prepared by conventional techniques. Typically, a small vertebrate such as a mouse, is hyperimmunized with the antigen. Specific methods of immunization are well known and are amply described in the literature and therefore, only one exemplary protocol will be briefly described here. The antigen preparation is injected with or without adjuvants into the mammal, followed by repeated injections over relatively short periods of time. To insure hyperimmunization, from two to six subsequent booster injections are administered. The animals are then killed, usually several days after the final injection, the spleens removed, and the spleen cells immortalized.

The manner of immortalization is not critical. Presently, the most common manner of achieving immortalization is through fusion with a myeloma cell fusion partner, which method is exemplified in the Experimental section herein. Other suitable techniques include EBV transformation, transformation with bare DNA, e.g., retroviruses, etc., or any other method which provides for stable maintenance of the cell line and production of monoclonal antibodies.

Once antibodies having suitable specificity have been prepared, a wide variety of immunological assay methods are available. Numerous competitive and non-competitive protein binding assays have been described in the scientific and patent literature, and a large number of such assays are commercially available. Exemplary immunoassays which are suitable for detecting the LDL subspecies in serum include those described in U.S. Pat. Nos. 3,791,932; 3,817,837; 3,839,153; 3,850,752; 3,850,578; 3,853,987; 4,034,074; and 4,098,876. Serum samples will typically be prepared by clotting whole blood samples and isolating the supernatant in accordance with conventional techniques. Optionally, prior to assaying, the LDL fraction in the serum sample may be separated by ultracentrifugation and gel electrophoresis, as described in the Experimental section hereinafter. Such fractionation increases the sensitivity of the assay.

Particularly preferred are sensitive enzyme linked immunosorbent assay (ELISA) methods which are described in detail in U.S. Pat. Nos. 3,690,874; 3,791,932; 3,850,752; 3,879,262; and 4,034,074. According to one such ELISA technique, the marker LDL is bound either covalently or non-covalently to a solid surface. After washing the surface to remove weakly-bound and unbound proteins, the serum sample is exposed to the surface in an appropriate buffer, and combined with the monoclonal antibodies specific for the particular subspecies of LDL. After incubating for sufficient time to allow binding of the LDL to the antibodies, labelled antibodies specific for the monoclonal antibodies, usually anti-mouse antibodies, are then added. Thus, the amount of bound label is directly proportional to the amount of LDL in the serum sample. Specific techniques for performing the immunoassays are set forth in the Experimental section hereinafter.

In the Experimental section hereinafter, the preparation of a particular hybridoma (SPL.IVA5) producing antibody (IVA5) specific for a unique determinant site on the characteristic LDL is described. Although the IVA5 antibody is found to preferentially bind sera from patients suffering from HTG, the antibody does display cross-reactivity with normal patient sera. Thus, when employing the particular IVA5 antibody, it is useful to provide a control to assure that any observed binding results from the presence of the characteristic LDL. For example, sera from normal individuals can be used as a control. Antibody IVA5 will bind patient sera at much higher dilutions than control sera. Many other suitable controls can be provided.

The following examples are offered by way of illustration, not by way of limitation.

EXPERIMENTAL

All percentages are by weight unless otherwise indicated. The following abbreviations are used:
BSA—bovine serum albumin
DMSO—dimethylsulfoxide
$EC_{50}$13 50% coating efficiency
ELISA—enzyme-linked immunosorbent assay
FCS—fetal calf serum
HAT—hypoxanthine-aminopterin-thymidine
HT—hypoxanthine-thymidine
HTG—hypertriglyceridemia
IDL—intermediate density lipoprotein
IMDM—Iscove's modified Dulbecco's medium
LDL—low density lipoprotein
$Na_2EDTA$—ethylenediaminetetraacetic acid disodium salt
PBS—phosphate-buffered saline
PEG—polyethylene glycol
RIA—radioimmunoassay
S—sedimentation units
SDS—sodium dodecylsulfate
$S_f$—sedimentation rate
VLDL—very low density lipoprotein.

METHODS

Preparation of Immunizing Antigen

A clinically normal male subject with no family history of coronary artery disease was employed as donor for preparation of immunizing antigen. Selection criteria included:

(1) The presence of several discrete LDL subspecies as determined by analytical ultracentrifugation and polyacrylamide gradient gel electrophoresis.

(2) Predominance of apolipoprotein B-containing LDL of normal size (240–290Å) and buoyant density (d=1.019–1.063 g/ml; $S_f \approx$ 0–12 S) as determined by SDS-polyacrylamide gradient gel electrophoresis.

(3) Detectable presence of an abnormally small LDL (215–230Å; $S_f \approx$ 0.3 S) resembling that seen in patients with $HTG_4$.

Plasma was collected into $Na_2EDTA$ (1 mg/ml) by plasmaphoresis after overnight fast. A total LDL fraction (d=1.019–1.063 g/ml) was prepared from plasma by preparative and density gradient ultracentrifugation as described by Shen et al. (1981) J. Lipid Res. 22:236–244. Electrophoretically homogeneous subspecies of this LDL fraction were isolated from the resulting gradient by high resolution density gradient fractionation using an ISCO Model 640 fraction collector in parallel with a Model UA-5 optical unit. Fractions were stored under nitrogen at 4° C. with $Na_2EDTA$ (1 mg/ml). Antigens prepared for long-term use as reference standards were flash frozen in a dry ice-acetone bath and stored at −70° C. in single-use vials. Sodium azide (0.1%), $Na_2EDTA$ (1 mg/ml) and nitrogen were used as preservatives. Fractions employed for immunization and screening were:

| Antigen | Designation | Particle Diameter (Å) |
|---|---|---|
| Total LDL | LDL | 215–290 |
| Major LDL Peak | Band III LDL | 250 |
| Minor LDL Peak | Band II LDL | 260 |

Polyclonal antisera generated in mice against LDL, Band II LDL and Band III LDL displayed superimposable dilution curves when screened against each antigen, and for that reason only LDL-immunized mice were used for fusion. Rabbits immunized with LDL were used as a source of polyclonal anti-human LDL antisera for direct two-site ELISA of human plasma.

Immunization

Animals received primary immunization one week after plasmaphoresis. Prior to immunization, antigens were clarified by microfugation, diluted in saline and emulsified in Freund's complete adjuvant by sonication (five 10-second bursts) with a cuphorn probe at a power setting of 5 (Branson Sonifier Cell Disruptor). Each of two weaned female New Zealand white rabbits was injected intradermally in multiple nodal regions with emulsified LDL (50–100 μg protein). Nine six-week old female Balb/c mice were similarly injected with 50–100 μg emulsified protein. Three mice were immunized with LDL; three mice were immunized with Band II LDL; and three were immunized with Band III LDL. Over the subsequent six weeks, each animal received two secondary immunizations with the same antigen preparation as the primary injection. Four days prior to sacrifice, LDL-immunized mice received a final intravenous injection of 50–100 μg native LDL protein (LDL, Band II LDL or Band III LDL) diluted in saline alone.

Isolation of Spleens

The three Balb/c mice immunized with LDL were sacrificed by cervical dislocation, bathed in Wescodyne and rinsed in 70% ethanol. Spleens were gently isolated using sterile surgical technique, freed of obvious fat and connective tissue, and washed three times by successive transfer through 60 mm petri dishes containing three ml serum-free IMDM containing 1% kanamycin sulfate (10 mg/ml). Spleens were placed in a dry 60 mm petri dish and carefully teased into pieces about 1 mm$^3$ using sharp-tipped forceps. Cells were collected by repeatedly rinsing the dish with serum-free IMDM plus kanamycin and pooled in 15 ml conical centrifuge tubes. Large pieces of tissue were pelleted by centrifugation at 500 rpm for 15–30 seconds. Supernate cells were transferred to fresh tubes. Spleen cells were then washed three times by centrifugation at 800–1000 rpm for five minutes through serum-free IMDM (10 ml/wash/spleen equivalent). Pellets were gently resuspended with an automated pipette (Pipet-aid; Drummond Scientific Co.) and pooled. Cells in the final suspension were counted at 1/50 and 1/100 dilutions on a Neubauer hemacytometer (American Optical Co.) after red cells had been lysed in 0.17M NH$^4$Cl.

Preselection of Myelomas

Mouse myelomas (SP 2/0 and P3X63AG8.653) were subjected to three selection processes before fusion with spleen cells from mice immunized with human LDL. Myelomas were first selected for resistance to 8-azaguanine to eliminate HGPRT$^+$ revertants. Cells were then selected for optimal growth in supplemented medium to maximize survival of hybrids in post-fusion HAT medium (complete medium+HAT). Finally, cells were adapted for growth in spinner flasks in volumes up to one liter. The preselection procedure is briefly detailed below.

Myelomas were expanded to $6\times10^5$ cells/ml in complete medium (IMDM salts plus 20% fetal calf serum, $5\times10^{-5}$ M 2-mercaptoethanol, 1% kanamycin sulfate (10 mg/ml), $10^{-4}$M 8-azaguanine, $10^{-4}$M hypoxanthine and $3\times10^{-5}$M thymidine) in T-150 (150 cm$^2$) flasks. Cells were then transferred to one-liter spinner flasks and supplemented with 100 ml fresh medium containing HT but not 8-azaguanine. Spinner cultures were maintained at 37° C., 5% CO$_2$ and 98% relative humidity with constant spinning at 50–60 rpm. Total and viable cell counts were monitored daily by trypan blue exclusion using a Neubauer hemacytometer. Cells were sustained in log phase by feeding or transferring cultures at a density of $8\times10^5$ cells/ml. Spinner-adapted myelomas in log phase were centrifuged at 1000 rpm, resuspended in one ml freeze medium (seven parts complete medium: two parts FCS: one part DMSO) per $10^7$ cells and frozen by cooling at a rate of 1° C./min to −70° C. in cryotubes (Nunc, Wheaton, Costar) containing one ml aliquots of the cell suspension. Cells were thawed with gentle swirling at 37° C., centrifuged at 1000 rpm through 10 ml complete medium and expanded to an appropriate volume of log phase cells prior to fusion.

Myeloma Cell Preparation

Myelomas were transferred from spinner cultures to 200 ml centrifuge bottles and centrifuged at 2000 rpm for five minutes. Pellets were pooled and washed three times by centrifugation through serum-free IMDM (1500 rpm for five minutes) in 50 ml conical centrifuge tubes. Cells were resuspended to approximately $10^7$ cells/ml with serum-free IMDM and counted by trypan blue exclusion.

Fusion

Spleen cells and myeloma cells were combined at a ratio of two spleen cells to five myelomas and centrifuged at 500–800 rpm for five minutes in 15 ml conical centrifuge tubes. Serum-free IMDM was aspirated, leaving a trace meniscus over the pellet. Pellets (0.8 ml) were resuspended by tapping. An equal volume of fusing solution (50% PEG for P3X63 cells, 40% PEG for SP 2/0 cells) was added dropwise with gentle tapping over a three minute interval at room temperature. The resulting suspension was centrifuged at 800 rpm for four minutes. Serum-free IMDM was then added to a volume of 10 ml with tilting and gentle shaking sufficient to dilute the PEG without disturbing the pellet. Tubes were centrifuged for five minutes at 500 rpm, and the supernatant was aspirated. Fused cells were stepwise resuspended in complete IMDM (10 ml) over a two minute interval.

Plating Fused Cells

The suspension of fused cells was diluted to yield $5\times10^4$ myeloma parents per 100 μl 50% macrophage-conditioned medium (one part macrophage-conditioned complete medium plus one part fresh complete medium containing HT). One hundred microliters of the final hybrid-containing media was dispensed into 96-well flat-bottomed dishes (corning or Costar) with a Bellco Mini-Spense II system. Approximately 36 hours after plating cells, 100 μl 50% macrophage-conditioned media containing HT plus $1.6\times10^{31}$ $^6$M aminopterin was added to each well with the Mini-Spense.

Screening and Expansion of Hybridomas

Viable colonies were scored as they appeared from eight to 21 days after fusion. When colonies were clearly visible to the naked eye and phenol red-containing media began to turn yellow with decreasing pH, aliquots of media were withdrawn and centrifuged to eliminate cell debris. Supernatants were assayed by solid phase RIA and ELISA. Over 600 hybridomas were repeatedly screened against stored aliquots of immunizing antigen as a test for secretion of anti-LDL antibody. Eighty nine cultures, including 80 which tested anti-LDL positive in initial screens, were successively expanded in complete medium without HT or aminopterin from 96-well plates (200 μl) to 24-well plates (1.5 ml) to 25 cm² flasks (5 ml) and finally to 75 cm² flasks (10–25 ml). Clarified media were assayed against immunizing antigen at each stage of expansion. Media from 75 cm² flasks were screened against Band II LDL, Band III LDL and a 1.019–1.063 g/ml LDL preparation from a patient with HTG4 as well as immunizing LDL. Each hybridoma was subsequently screened against fresh or appropriately stored ($-70°$ C.) LDL preparations from seven blind controls and two patients with HTG4. VLDL and IDL were also used as screening antigens, but these lipid-rich preparations were found to be highly unstable with routine storage.

Multiple replicates of each hybridoma were frozen as cultures and approached densities of $10^6$ cells/ml in 75 cm² flasks. Log phase cells were centrifuged at 1000 rpm for five minutes, resuspended at approximately $10^7$ cells/ml freeze medium six parts FCS to three parts complete medium to one part DMSO), cooled to $-70°$ C. at a rate of 1° C./minute in one ml aliquots (Nunc, Wheaton or Costar cryotubes) and stored at $-150°$ C.

Subcloning by Limiting Dilution

Hybridomas of interest were twice subcloned by limiting dilution to ensure monoclonality with $>99.5\%$ confidence. Aliquots of hybridoma-containing media were diluted in complete medium to yield 0.5 cell/ml 50% macrophage-conditioned medium. Two hundred microliter aliquots of the cell suspension were dispensed into 96-well plates (Costar) to yield a mean cell density of one cell per 10 wells. As colonies appeared between day eight and 18, subclones were expanded successively from 96-well plates through 25 cm² flasks. Each subclone was screened in varying dilution against control and HTG$^4$ LDL. Dilution curves for all subclones from a given parent culture were mutually superimposable. Subcloned cultures were frozen from 25 cm² flasks at densities of approximately $5 \times 10^6$ cells/ml freeze medium.

Analytical Methods

Preparative and analytical ultracentrifugation were performed by methods of Shen et al., supra., and Lindgren et al., AOCS Conference of Dietary Fats and Health, Perkins and Visek, eds., Chicago, 1981. Polyacrylamide gradient gel (2–16%) electrophoresis and SDS-polyacrylamide gradient gel (4–30%) electrophoresis were performed by methods of Krauss and Burke (1982) J. Lipid Res. 23:97–104 and Kane et al. [insert citation], respectively. Antigens were transferred from 2–16% gradient gels (Pharmacia) to nitrocellulose paper (Schleicher & Schuell BA85) by methods modified from those of Burnette [insert citation]. Transfers were performed over 12 hours at a constant current of 150 mA in a Bio-Rad Trans-Blot apparatus. Blots were fixed in 0.05% acetic acid for 2–12 hours at 4° C. and blocked for three hours at 37° C. in phosphate-buffered saline containing 30 mg/ml bovine serum albumin (Sigma Fraction V) prior to immunoperoxidase staining (Burnette, supra). Diaminobenzidine and 4-chloro-1-napthol (Sigma) were used as peroxidse substrates. Lipoprotein particle sizes were determined by scanning densitometry using a Transidyne RFT densitometer Krauss and Burke, supra. Gels were scanned at 530 nm in the transmission mode using Pharmacia high molecular weight standards and latex beads sized by electron microscopy to construct a standard curve relating migration distance to particle diameter. Immunoperoxidase-stained nitrocellulose blots were scanned at 530 nm in the reflectance mode using sizing standards from corresponding gels. Methods for quantitating immunoglobulins in hybridoma media and lipoproteins in human plasma are discussed elsewhere (Cubicciotti et al. [insert citation]).

Antibody Enrichment

High-titer preparations of each relevant hybridoma were generated in the form of ascites fluids and ammonium sulfate precipitates. Ascites fluids were generated by injecting balb/c mice intraperitoneally with $1.5 \times 10^7$ hybridoma cells in 200 μl complete medium two weeks after priming animals with 0.5 ml pristane. Mice were tapped intraperitoneally for ascites fluid on the 7th, 9th and 11th days after injection of cells. Fluids were clarified by centrifugation (1500 rpm for six minutes), and residual pristane was pipetted off. Mouse-conditioned hybridomas were produced by reculturing cells pelleted from ascites fluids which had been removed from animals under sterile conditions. Ascites fluids exhibited a 200-fold enrichment of antibody relative to untreated culture media.

Ammonium sulfate cuts were performed by addition of 288 gm/l ultra-pure ammonium sulfate (Schwarz-Mann) to clarified hybridoma media at 4° C. with stirring over two hours. Antibody was precipitated by centrifugation for 30 minutes at 8000 rpm, resuspended in 50 ml 0.05 M Tris-HCl (pH 7.5) and dialyzed against the same buffer for three days with seven changes of dialysis buffer. This procedure yielded approximately 15-fold antibody enrichment.

Hybridoma media, ascites fluids and ammonium sulfate precipitates were routinely stored at $-20°$ C. and clarified by centrifugation prior to use. Dilution curves for different preparations of a given hybridoma-generated antibody exhibited identical slopes and maxima. Unless otherwise specified, results refer to experiments conducted with untreated hybridoma media.

Hybridoma Screening during Expansion

Each hybridoma was screened for anti-LDL antibody secretion at each stage of expansion by both solid phase RIA and ELISA.

RIA was performed with $^{125}$I-conjugated goat anti-mouse IgG as the secondary antibody. Immulon I removable strips (Dynatech) were placed in holders. Wells were coated overnight at 4° C. with 500 ng lipoprotein (LDL, VLDL, IDL) in 200 μl carbonate-bicarbonate buffer (pH 9.6). The wells were washed three times with PBS-Tween ®-BSA (PBS containing 0.05% Tween ® 20 and 2 mg/ml Fraction V BSA (Sigma)). Clarified hybridoma medium (200 μl) diluted in PBS-Tween ®-BSA was applied to each well including appropriate first and second antibody controls. After incubation for two to five hours at room temperature, the wells were washed three times with PBS-Tween ®-BSA, and $^{125}$I-conjugated goat anti-mouse IgG (200 μl diluted in PBS-Tween ®-BSA to 50,000 cpm/well) was applied to each well. After additional incubation for two to five hours at room temperature, the cells were washed three times with PBS-Tween ®-BSA, aspirating between washes. The edges and bottoms of wells were wiped dry with Kimwipes and individual wells counted in Beckman gamma counter.

ELISA was performed with the following secondary antibodies:
(a) goat anti-mouse alkaline phosphatase (Sigma) (substrate=p-nitrophenyl phosphate),
(b) goat anti-mouse beta-galactosidase (Zymed) (substrate=p-nitrophenyl-beta-galactopyranoside), and
(c) goat anti-mouse peroxidase (Zymed) (substrate=0-dianisidine).

Immulon I flat-bottomed 96-well microtiter plates were coated overnight at 4° C. with 500 ng lipoprotein per well in 200 μl carbonate-bicarbonate buffer (pH 9.6). After washing three times with PBS-Tween ®-BSA, clarified hybridoma medium (200 μl) diluted in PBS-Tween ®-BSA was applied to each well. After incubation for two to five hours at room temperature, the wells were washed three times with PBS-Tween ®-BSA, and secondary antibody (200 μl) diluted 1/1000 in PBS-Tween ®-BSA added to each well. After additional incubation for two to five hours at room temperature, the wells were washed three times with PBS-Tween ®-BSA, and substrate (200 μl) added to each well. Optical density was read at 405 nm or 450 nm (peroxidase) as a function of time in Titer-Tek Multiskan and the rate of substrate turnover calculated.

Immunoperoxidase Staining of Nitrocellulose Transfers

Nitrocellulose transfers from 2–16% gradient polyacrylamide gels of plasma samples (three μl) from two control subjects and one patient with $HTG_4$ were challenged with 1/20 dilutions of media from 12 selected hybridomas and stained with goat anti-mouse peroxidase using diaminobenzidine as substrate. Six of these media were reexamined by immunoperoxidase staining of nitrocellulose transfers from gels of another $HTG_4$ patient and three other control subjects using 4-chloro-1-napthol as substrate. After blocking for three hours at 37° C. in phosphate-buffered saline containing 3% bovine serum albumin, nitrocellulose transfers were incubated for three hours at 37° C. with hybridoma media diluted in blocking buffer. Blots were then transferred to fresh dishes, washed four times (15 minutes) in PBS at room temperature and incubated in goat anti-mouse horseradish peroxidase (1/1000 in blocking buffer) for three hours at room temperature. Transfers were washed four times with phosphate-buffered saline and stained with substrate. Stained blots were scanned with a Transidyne RFT densitometer and photographed for permanent record.

Antibody Characterization by Microplate Enzyme Immunoassay

Among hybridoma media screened by conventional RIA, ELISA and immunoperoxidase staining of nitrocellulose transfers, three were selected as potentially useful probes for different epitopes of human LDL. These hybridoma media were subtyped by direct ELISA using Zymed type-specific rabbit anti-mouse antisera according to Zymed recommendations. In addition, several different types of ELISA were designed to examine the nature of interaction between each secreted antibody and its respective lipoprotein epitope. Relevant methods are described below.

1. Direct ELISA 1

Dilution curves for each hybridoma media against patient ($HTG_4$) and control LDL were obtained by direct ELISA as outlined above. Media were assayed at dilutions ranging from $10^{-4}$ to $3 \times 10^{-1}$. Ascites fluids were assayed at dilutions ranging from $10^{-6}$ to $10^{-1}$. First and second antibody incubations were set at two hours. Goat anti-mouse alkaline phosphatase and goat anti-mouse beta-galactosidase were used as second antibodies. Rates of substrate turnover were determined over 60 minute and 180 minute intervals for the alkaline phosphatase and beta-galactosidase assays, respectively.

2. Direct ELISA 2

Time courses of antibody-antigen interaction were evaluated by direct alkaline phosphatase ELISA as above with first antibody incubations ranging from 10 seconds to 60 minutes.

3. Direct ELISA 3: Human Plasma

Recognition by hybridoma media of lipoprotein epitopes in human plasma was confirmed by direct two-site ELISA. Immulon II plates were coated overnight with 100 μl/well of monoclonal culture medium diluted 1/50 in a carbonate-bicarbonate buffer (pH 9.6). Plates were washed three times with PBS-Tween ®-BSA with a one hour blocking step at room temperature. One hundred microliters of human plasma diluted from $2 \times 10^{-1}$ to $10^{-3}$ in PBS-Tween ®-BSA was added to each well and left at room temperature for two hours. Plates were washed three times with PBS-Tween ®-BSA, incubated with 100 μl/well rabbit anti-human LDL antisera (1/200 dilution in PBS-Tween ®-BSA) for two hours at room temperature and washed again. One hundred microliters goat anti-rabbit alkaline phosphatase diluted 1/1000 in PBS-Tween ®-BSA was then added to each well. After a two hour incubation at room temperature, plates were washed three times with PBS-Tween ®-BSA, and 200 μl substrate (Sigma substrate tablets in diethanolamine buffer, pH 9.6) was added to each well.

4. Indirect ELISA 1: LDL Competition

Specificity of antibody-LDL interaction was demonstrated by including an LDL competition step in the direct ELISA. Plates were coated overnight with 500 ng (or variable amounts) LDL/well in 100 μl carbonate-bicarbonate buffer (pH 9.6). Variable dilutions of hybridoma medium were preincubated with variable dilutions of LDL ($0-10^4$ ng protein) for two hours at room temperature with shaking (PBS-Tween ®-BSA as diluent). Plates were washed three times with PBS-Tween ®-BSA with a one hour blocking step at room temperature. Samples were vortexed, and 100 μl aliquots were applied to wells. Incubations were performed at room temperature for two hours with gentle shaking. Plates were washed and incubated with second antibody and substrate as described for "Direct ELISA 1".

5. Indirect ELISA 2: Plasma Competition

The assay is performed as described for "Indirect ELISA 1", except that dilutions of human plasma ($10^{-4}$ to $10^{-1}$ in PBS-Tween ®-BSA) are used in place of LDL in the competition step.

6. Indirect ELISA 3: Quasi-Competition

This assay permits examination of antibody-antigen interaction in the liquid phase by allowing antigen-independent attachment of free antibody to plates. Immulon II plates were coated overnight at 4° C with rabbit anti-mouse $IgG_1$ antisera (Cappel) diluted 1/500 in a carbonate-bicarbonate buffer (pH 9.6). Variable dilutions of hybridoma media were preincubated with gentle shaking for two hours at room temperature with variable dilutions of human plasma in PBS-Tween ®-BSA. Plates were washed three times with PBS-Tween ®-BSA with a one hour blocking step. Preincubated samples were vortexed and 100 μl aliquots were added to wells. Second antibody and substrate steps were performed as described for "Direct ELISA 1".

7. Quantitative ELISA

The concentration of immunoglobulin in culture media, ascites fluids or ammonium sulfate-precipitated antibody preparations was determined by direct ELISA. Plates were coated overnight at 4° C. with 100 μl of rabbit anti-mouse subtype-specific antisera (Miles, Cappel) and washed three times with PBS-Tween ®-BSA with a one hour blocking step. Variable dilutions of affinity-purified mouse myeloma-produced subtype-specific antibody or unknown antibody preparation (of known subtype) were added to wells in 100 μl PBS-Tween ®-BSA and allowed to incubate at room temperature for two hours. Plates were washed and incubated with second antibody and substrate as described for "Direct ELISA 1". Standard myeloma protein curves were constructed by normalizing rates as percent of maximum. Dilution curves for unknowns were constructed by normalizing rates to a theoretical maximum determined by mixed-order kinetic analysis. Dilution curves for unknowns were compared to standard curves by a correlative plot. Lipoproteins in human plasma can be quantitated by performing this assay in combination with a quasi-competition ELISA on the same plate.

RESULTS

Lipoprotein Studies

Preparative and analytical ultracentrifugation of LDL immunizing antigen obtained from the clinically normal subject revealed at least three distinct subpopulations in the 1.019–1.063 g/ml density gradient. Heterogeneity of the resulting LDL preparation was further evidenced by polyacrylamide gradient gel electrophoresis of immunizing LDL and whole plasma from which it was derived. At least five discrete peaks or shoulders were discernible in the LDL size range (240–290Å). Major peaks span the 245–265Å size range, but trace amounts of LDL sized at 223Å were also apparent.

Electrophoretic data for two HTG$_4$ patients and three control subjects revealed that each patient had a prominent LDL subspecies in the 215–230Å size range, while the principal LDL species for control subjects are in the 260–270Å size range.

Gradient gel scans of whole plasma from 16 clinically normal individuals and 25 hypertriglyceridemic patients were performed. Each patient scan revealed LDL subspecies in the 215–230Å size range, while scans for control subjects were lacking in LDL of that size. These findings are consistent with reported inverse correlations between LDL material of S$_f$ (0–7) and HDL cholesterol (Krauss et al., supra.).

Hybridomas

Forty-four 96-well tissue culture plates (Corning, Costar, Falcon) were seeded with $5 \times 10^4$ SP 2/0 myeloma parents and $2 \times 10^4$ B-lymphocytes per well. Viable colonies were detected in 7.5% of seeded wells by day 21. Sixty seven (21%) of 316 viable colonies were shown to secrete anti-LDL antibody by repeated RIA and ELISA using a variety of conjugated second antibodies (see "Methods").

Forty three 96-well tissue culture plates were seeded with $5 \times 10^4$ P3X63AG8.653 myeloma parents and $2 \times 10^4$ spleen cells per well. Viable colonies (254) were detected in 6.1% of seeded wells by day 21. Thirteen of these hybridomas tested anti-LDL positive by microplate enzyme immunoassay.

Eighty nine hybridomas, including eighty which tested anti-LDL positive, were expanded and frozen as described in "Methods". Antibodies secreted by twelve of these hybridomas were characterized in detail by microplate enzyme immunoassay and immunoperoxidase staining of nitrocellulose transfers from whole plasma polyacrylamide gradient gels. Results for hybridomas SPL.IID2, SPL.IVA5 and SPL.IVB5 are presented below. Hybridomas and secreted antibodies are referred to in accordance with the following system of nomenclature:

| Parent Hybridoma | Antibody | Subcloned Hybridoma | Antibody |
|---|---|---|---|
| SPL.IID2 | IID2 | SPL.IID2A2 | IID2A2 |
| SPL.IVA5 | IVA5 | SPL.IVA5A1 | IVA5A1 |
| SPL.IVB5 | IVB5 | SPL.IVB5A1 | IVB5A1 |

Unlike hybridomas SPL.IID2 and SPL.IVB5, SPL.IVA5 tested anti-LDL negative in preliminary screens using immunizing LDL as antigen. Subsequent screening assays suggested that SPL.IVA5 does secrete anti-LDL antibody and that the order of potency of IVA5 against a panel of antigens differs from IID2 and IVB5 as follows:

| Hybridoma | Initial Screen Immunizing LDL | Subsequent Screens | | | |
|---|---|---|---|---|---|
| | | LDL | Band II | Band III | Patient LDL |
| SPL.IID2 | +++ | +++ | +++ | +++ | +++ |
| SPL.IVA5 | − | − | − | − | +++ |
| SPL.IVB5 | ++ | ++ | + | ++ | ++ |

Hybridomas SPL.IID2, SPL.IVA5 and SPL.IVB5 are stable cell lines currently stored in liquid nitrogen at the Naval Biosciences Laboratory, Oakland, CA. Cell line SPL.IVA5 was also deposited at the American Type Culture Collection, 12301 Parklawn Drive, Rockville, Md. 20852, on Mar. 29, 1984, and granted accession no. HB8535. Each hybridoma has been tested as stable in culture for at least 60 days without detectable change in antibody output. In addition, each hybridoma is stable to cryopreservation (at least nine months at −150° C.). Finally, each hybridoma is stable to subcloning by limiting dilution using a seeding density of one cell/10 wells. Subcultures from three successively subcloned generations of each hybridoma displayed mutually indistinguishable dilution curves against LDL from control subject (n=2) or patients with HTG$_4$ (n=2). Since each round of subculturing yielded a mean of nine viable colonies per 96-well plate seeded, antibodies IID2A2, IVA5A1 and IVB5A1 are monoclonal with 99.9% confidence.

Antibody Specificity

Attachment of control and patient LDL to Immulon I microtiter plates was dose-dependent as assessed by rate of alkaline phosphatase ELISA in which variable amounts of LDL (0.01–2.0 μg/well) were challenged with a given amount ($10^{-4}$, $10^{-3}$ or $10^{-2}$ dilution) of first antibody (hybridoma medium). The alkaline phosphatase response to a $10^{-2}$ dilution of IVA5 was saturable, plateauing at approximately 500 ng LDL protein/- well. By contrast, binding of antibody IVA5 to variable amounts of patient LDL was not saturable within the range of LDL concentrations studied. Maximal binding of antibodies IID2 and IVB5 to plates coated with variable amounts of LDL could be demonstrated at 200-500 ng LDL protein/well. Since either coating efficiency or epitope exposure appears to vary depending upon the LDL preparation and antibody used, direct ELISA was routinely performed under conditions of antigen excess by coating plates with 500 ng LDL protein.

Antibodies IID2, IVA5 and IVB5 were each determined to be immunoglobulins of type $IgG_1$ with kappa light chains (see "Methods"). Concentrations of immunoglobulin in culture media and ascites fluids were determined by direct quantitative ELISA as described in "Methods". Correlative analysis of standard vs. unknown curves ($\mu g$ $IgG_1$ vs. $\mu l$ IVA5A1) revealed that IVA5A1 contains approximately 20 $\mu g$ $IgG_1$/ml culture medium. Hybridoma IVA5A1 contains approximately 20 $\mu g$ $IgG_1$/ml. Ascites fluids generated by injecting pristane-primed mice with $1.5 \times 10^7$ hybridoma cells (SPL.IID2A2, SPL.IVA5A1 or SPL.IVB5A1) were found to contain $IgG_1$ in concentrations of 2 mg/ml (IVB5A1) and 4 mg/ml (IID2A2, IVA5A1), representing 100- and 200-fold antibody enrichment, respectively. These results are reinforced by the finding that dilution curves for IVB5A1 culture media and ascites fluids exhibited a 100-fold difference in $EC_{50}$, while 200-fold differences were observed for IID2A2 and IVA5A1. Slopes of dilution curves for ascites fluids and culture media were identical in each case. Reciprocal plots (1/rate vs. 1/dilution) for $IgG_1$ standards and hybridoma media were linear over the range of 0.2-20 ng $IgG_1$/well. These results suggest that:

(1) IID2A2 and IVA5A1 have similar avidities for their respective binding sites.

(2) IVB5A1 has a lower avidity for its LDL binding site than either IID2A2 or IVA5A1.

(3) The number of LDL binding sites recognized by IVA5A1 is greater than the number recognized by either IID2A2 or IVB5A1.

Binding of IID2, IVA5 and IVB5 to Immulon I plates coated with 500 ng LDL protein/well was saturable and dose-dependent. The specificity of each antibody for control and patient LDL was evaluated by direct ELISA in which wells coated with 500 ng control LDL (n=2) or patient LDL (n=2) were challenged with variable dilutions of hybridoma media. Antibody IVA5 recognized patient LDL at dilutions of culture medium which were subthreshhold against control LDL. As a result of plotting these results, the curve for patient LDL is upwardly displaced and left-shifted relative to the control LDL curve, indicating that patient LDL has either more abundant or higher avidity binding sites for IVA5 than control LDL. Antibodies IID2, and IVB5, by contrast, exhibited dilution curves for patient and control LDL which were superimposable over dilutions ranging from $10^{-4}$ to $10^{-2}$. These results suggest that IVA5 recognizes with high avidity an epitope of LDL which occurs in plasma from $HTG_4$ patients and not in control plasma.

In view of these findings, it appeared that preferential recognition of patient LDL by IVA5 could be explained by high affinity binding to an epitope of LDL located on the 215-230Å LDL not present in control plasma. This hypothesis was tested by immunoperoxidase staining of nitrocellulose transfers from polyacrylamide gradient gels (Pharmacia, 2-16%) of plasma samples (4 $\mu l$) from control subjects (n=5) and patients with $HTG_4$ (n=2). Immunoperoxidase staining (4-chloro-1-napthol as substrate) of blots challenged with a 1/20 dilution of IVA5 revealed that this antibody recognized a 215-230Å LDL subspecies in patient plasma in addition to LDL in the normal size range (240-290Å). Antibody IID2, by contrast, bound predominantly to lipoproteins in VLDL (>360Å) and IDL-LDL (260-300Å) size ranges, while IVB5 was relatively specific for normal LDL of 255-265Å (particle diameters determined by scanning densitometry of stained blots in reflectance mode; see "Methods"). The outer lane adjacent to the patient plasma lane of each gel was loaded with isolated patient LDL (2 $\mu l$). A single band (225Å) in this lane displayed a corresponding band in the patient plasma lane, and both were recognized by IVA5 only. These results, combined with the observation that the small LDL band appeared most rapidly after addition of peroxidase substrate, reinforce the observation that high avidity binding of IVA5 to small LDL in patient plasma accounts, at least in part, for differences between control and patient dilution curves.

The specificity of IID2, IVA5 and IVB5 for LDL in contrast to other plasma constituents was tested by indirect (competition) ELISA as described in "Methods". Competition was observed with over the range of 0.1-10 $\mu g$ LDL protein/well. Half-maximal competition of 1/500 dilutions of IVA5 and IVB5 occurs at 300-800 ng LDL/well, in good agreement with the amount of LDL required to half-maximally saturate Immulon I wells (150-200 ng).

It appears, thus, that ELISA-determined activity of IID2, IVA5 and IVB5 against human LDL represents specific, saturable binding of antibody to antigen. If the avidity and specificity of these antibodies is sufficiently great, it should be feasible to detect and quantitate recognized epitopes by indirect ELISA of human plasma without tedious isolation of LDL. Furthermore, if IVA5 recognizes 215-230Å patient LDL with higher avidity than control LDL, lesser amounts of patient than control plasma should be required to compete by indirect ELISA for this antibody in the liquid phase. To test this hypothesis, competition ELISA's were performed by preincubating hybridoma media (1/200 dilution) with variable dilutions of plasma from control subjects (n=6) and hypertriglyceridemic patients (n=8). Whether wells were coated with control or patient LDL (500 ng), the patient plasma competition curve was left-shifted 2.5-fold relative to the control plasma curve. As expected, greater OD responses were obtained with uncompeted antibody when wells were coated with patient rather than control LDL. These findings have been confirmed in each subsequent trial. While substantial scatter was apparent among control curves, plasma samples from hypertriglyceridemic patients elicit virtually superimposable competition curves. No systematic differences among patient and control plasmas were detected in similar competition ELISAs using IID2 or IVB5 as first antibody. Results of similar experiments with preincubations and first antibody incubations performed at temperatures ranging from 4° to 37° C. were qualitatively similar to those performed at room temperature. Epitopes recognized by these antibodies, thus, appear to be relatively stable configurations on LDL rather than conformation-dependent determinants.

The hypothesis that antibody IVA5 recognizes patient LDL with greater avidity than control LDL was further tested by examining the time course of antibody binding by direct ELISA. If IVA5 recognizes 215–230Å patient LDL with higher avidity than control LDL, this difference should be most apparent during the initial rate phase of antibody-antigen interaction. Time course studies conducted over 3–60 minute intervals (first antibody incubation) exhibited non-zero intercepts. Early time course studies indicated that the initial rate phase of antibody-antigen was linear for less than three minutes at higher concentrations of antibody. Initial binding rates for IVA5 were two-fold greater in wells coated with patient LDL compared to control LDL at each concentration of antibody. Initial rates for antibodies IID2 and IVB5, by contrast, were virtually identical whether wells were coated with patient or control LDL. These findings further confirm the notion that antibody IVA5A1 recognizes with high avidity a particle present in patient plasma which does not occur in clinically normal individuals.

In accordance with the subject invention, sensitive assays are provided for detecting the presence of an immunologically distinct LDL subspecies in a patient's serum. The presence of that subspecies, in turn, is characteristic of type IV hypertriglyceridemia. Thus, the serum assay promises to have widespread application in screening for patients suffering from or susceptible to hypertriglyceridemia, which patients are particularly susceptible to heart attack and stroke.

Although the foregoing invention has been described in some detail by way of illustration and example for purposes of clarity of understanding, it will be obvious that certain changes and modifications may be practiced within the scope of the appended claims.

What is claimed is:

1. Hybridoma SPL.IVA5A1, A.T.C.C. accession no. HB 8535.

2. Antibodies derived from hybridoma SPL.IVA5, A.T.C.C. accession no. HB 8535.

3. A method for identifying the presence of low density lipoprotein characteristic of hypertriglyceridemia in a patient, said method comprising:

contacting a sample of a biological fluid from said patient with antibodies specific for the epitopic site recognized by antibodies derived from hybridoma SPL.IVA5, A.T.C.C. Accession No. HB 8535, which antibodies bind to a low density lipoprotein subspecies having a size in the range of about 215Å to 230Å for a time and under conditions sufficient for said low density lipoprotein subspecies and said antibodies to form an immune complex and detecting the presence or absence of said immune complex, wherein the presence of said immune complex is indicative of hypertriglyceridemia.

4. A method according to claim 3, wherein said monoclonal antibodies are derived from hybridoma SPL.IVA5, A.T.C.C. Accession No. HB 8535.

* * * * *